United States Patent
Ashton et al.

(10) Patent No.: US 6,764,478 B2
(45) Date of Patent: Jul. 20, 2004

(54) DISPOSABLE ABSORBENT GARMENT HAVING HIGHLY EXTENSIBLE LEG OPENINGS

(75) Inventors: Gregory Ashton, Cincinnati, OH (US); Eiro Fukuda, Cincinnati, OH (US); Frederick Michael Langdon, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 22 days.

(21) Appl. No.: 09/897,823

(22) Filed: Jun. 29, 2001

(65) Prior Publication Data

US 2003/0004488 A1 Jan. 2, 2003

(51) Int. Cl.[7] .............................................. A61F 13/20
(52) U.S. Cl. ...................... 604/385.25; 604/385.23; 604/385.24; 604/385.01; 604/396
(58) Field of Search ................. 604/385.23, 385.01, 604/396, 385.13, 385.21, 385.26, 373, 377

(56) References Cited

U.S. PATENT DOCUMENTS

| | | | |
|---|---|---|---|
| 3,860,003 A | | 1/1975 | Buell |
| 4,031,568 A | * | 6/1977 | Huff ............................... 2/402 |
| 4,205,679 A | * | 6/1980 | Repke et al. ................ 604/366 |
| 4,324,245 A | | 4/1982 | Mesek et al. |
| 4,610,681 A | | 9/1986 | Strohbeen et al. |
| 4,639,949 A | | 2/1987 | Ales et al. |
| 4,641,381 A | | 2/1987 | Heran et al. |
| 4,690,681 A | * | 9/1987 | Haunschild et al. ......... 604/396 |
| 4,695,278 A | | 9/1987 | Lawson |
| 4,701,175 A | * | 10/1987 | Boland et al. .......... 604/385.22 |
| 4,795,454 A | | 1/1989 | Dragoo |
| 4,808,176 A | | 2/1989 | Kielpikowski |
| 4,938,753 A | | 7/1990 | Van Gompel et al. |
| 4,938,757 A | * | 7/1990 | Van Gompel et al. .. 604/385.22 |
| 5,064,421 A | | 11/1991 | Tracy |
| 5,156,793 A | * | 10/1992 | Buell et al. ............... 264/288.8 |
| 5,204,997 A | | 4/1993 | Suzuki et al. |
| 5,542,943 A | | 8/1996 | Sageser |
| 5,577,540 A | | 11/1996 | Sageser |
| 5,735,838 A | | 4/1998 | Ronnberg et al. |
| 5,797,824 A | * | 8/1998 | Tracy ..................... 604/385.29 |
| 5,827,387 A | | 10/1998 | Reynolds et al. |
| 5,851,204 A | | 12/1998 | Mizutani |
| 5,891,122 A | | 4/1999 | Coates |
| 6,083,212 A | | 7/2000 | Kumasaka |
| 6,120,632 A | * | 9/2000 | Dragoo et al. ............... 156/164 |
| 6,168,585 B1 | | 1/2001 | Cesco-Cancian |
| 6,171,290 B1 | * | 1/2001 | Boisse et al. ........... 604/385.01 |
| 6,383,170 B1 | * | 5/2002 | Mishima et al. ........ 604/385.19 |
| 6,613,033 B1 | * | 9/2003 | Popp et al. ............. 604/385.25 |

FOREIGN PATENT DOCUMENTS

| | | | |
|---|---|---|---|
| EP | 0 591 647 B1 | 4/1994 | |
| EP | 1 064 895 A2 | 1/2001 | |
| EP | 1 072 243 A2 | 1/2001 | |
| EP | 1 080 708 A2 | 3/2001 | |
| WO | WO 93/03698 | 3/1993 | |
| WO | WO 94/18927 | 9/1994 | |
| WO | WO 97/12571 | 4/1997 | |
| WO | WO 98/29080 | 7/1998 | |
| WO | WO 99/56941 | 11/1999 | |
| WO | WO 99/60971 | * 12/1999 | ........... A61F/13/15 |
| WO | WO 01/00053 | 1/2001 | |
| WO | WO 01/00915 | 1/2001 | |
| WO | WO 01/34081 | 5/2001 | |

* cited by examiner

*Primary Examiner*—Henry Bernett
*Assistant Examiner*—Amanda Flynn
(74) *Attorney, Agent, or Firm*—Michael P. Hayden; Jay A. Krebs; Ken K. Patel

(57) ABSTRACT

Absorbent article having a containment assembly and highly extensible leg openings. The leg opening margins may have portions having differential properties, such as differential elastic extensibility. The absorbent article may also have highly extensible outer leg cuffs. Additionally, the absorbent article may have a narrow crotch region. The absorbent article may thus provide ease of application and removal, sustained dynamic fit, prevention of leakage, sustained wearer comfort, and desirable appearance.

33 Claims, 7 Drawing Sheets

DISPOSABLE ABSORBENT GARMENT HAVING HIGHLY EXTENSIBLE LEG OPENINGS

FIELD OF THE INVENTION

The present invention relates to absorbent articles such as diapers, incontinence briefs, pull-on diapers, training pants, diaper holders and liners, sanitary hygiene garments, and the like. More particularly, the present invention relates to absorbent articles providing ease of application and removal, sustained dynamic fit, prevention of leakage, sustained wearer comfort, and desirable appearance.

BACKGROUND OF THE INVENTION

When absorbent articles such as diapers and training pants are worn, gaps tend to form between the article and the body. Because leakage can occur through these gaps, the designs of absorbent articles typically include features intended to sustain the proper fit on the body. For example, the designs of many absorbent articles include leg cuffs located generally along the side edges which form the leg openings when the articles are worn. Leg cuffs, in general, are known variously in the art as leg cuffs, leg bands, side flaps, barrier cuffs, containment flaps, and/or elastic cuffs.

Outer leg cuffs are located distally from the longitudinal centerline, relative to other leg cuff elements that may be present, and typically have elastic elements sandwiched between layers of the materials making up a main structure of the article. This main structure is typically the containment assembly or a side structure which is attached to the containment assembly and which forms ears to give the overall article an hourglass shape. In general, the outer leg cuff elastic elements provide contractive forces tending to draw the materials against the legs and thus form gaskets to prevent leakage, while also providing a range of elastic extensibility to allow the absorbent article to be fitted onto the body of a wearer.

However, the shapes of absorbent articles are often distorted by elastic features. For example, the contractive forces of the elastic waist features, elastic side panels, and/or elastic leg cuffs tend to draw the distal edges of the leg openings upward and inward, thus effectively rotating the leg openings toward a longitudinal orientation. This longitudinal orientation makes the insertion of the wearer's feet and legs more difficult and especially aggravates the difficulty of application of pre-closed absorbent articles having inner leg cuffs, which tend to catch the wearer's feet and toes during insertion.

In some designs of absorbent articles, the upper edges of the leg openings are formed by the lower edges of elastic side panels. Because these elastic side panels often are designed to provide forces intended to support the article on the body of the wearer, the forces they provide may be ineffective in preventing gapping around the legs. Examples of designs having leg openings formed by elastic side panels are described in U.S. Pat. No. 4,938,757 issued to Van Gompel et al. on Jul. 3, 1990. The designs of some elastic side panels include angled elastic components having one end located on or near the front edge of the waist opening and another end located on or near the back edge of the leg opening. However, an elastic component which is angled downward toward the back exerts a downward force on the front portion of the article, which may lead to gapping around the leg openings. Examples of designs having side panels including angled elastic components are described in U.S. Pat. No. 5,669,897 issued to Lavon et al. on Sep. 23, 1997 and U.S. Pat. No. 5,899,895 issued to Robles et al. on May 4, 1999.

When an elastic leg cuff is designed to generate a high contractive force in an attempt to minimize gapping, the high force often causes discomfort to the wearer and/or creates pressure marks on the body. This problem is especially difficult to avoid in designs having outer leg cuffs containing elastic strands, which tend to exert concentrated forces on the wearer. The high contractive force may also tend to make application and/or removal of the article difficult.

The designs of some outer leg cuffs have the elastic components inset some distance from the edge of the leg openings. However, the inset elastic components of outer leg cuffs are typically incapable of drawing the actual edges of the leg openings against the legs of the wearer. As a result, the effectiveness of such outer leg cuffs as gaskets to prevent leakage is limited.

Another disadvantage of some typical designs of outer leg cuffs is that the appearance of the raw edges of the sheet or web materials surrounding the leg openings differs appreciably from that of a durable garment or of a disposable absorbent article having the garment-like appearance desired by many users. In attempts to improve the appearance, some absorbent articles have material wrapped over the edges of the leg openings, that is, folded over the edges of the materials. However, these designs have another disadvantage in that the added layers of materials tend to resist the contractive forces exerted by the elastic components. Examples of wrapped cuff designs are described in U.S. Pat. No. 6,171,290 issued to Boisse et al. on Jan. 9, 2001. In some designs, strips of soft padding material are wrapped over the edges of the leg openings. These designs have the same disadvantage of additional resistance to contraction. Examples of designs with soft padding are described in U.S. Pat. No. 5,064,421 and U.S. Pat. No. 5,797,824 both issued to Tracy on Nov. 12, 1991 and Aug. 25, 1998, respectively.

Thus, it would be beneficial to provide an absorbent article designed to sustain the proper fit of the article around the legs of the wearer. It would also be beneficial to provide an absorbent article having improved appearance around the legs. It would be of further benefit to provide an absorbent article having a reduced possibility of leakage at the legs. Additionally, it would be of benefit to provide an absorbent article having easy application and/or removal and, in particular, easy insertion of the feet and legs of a wearer into the leg openings of the article. And, it would be of benefit to provide an absorbent article also providing improved comfort for the wearer.

SUMMARY OF THE INVENTION

The present invention provides absorbent articles, such as diapers, incontinence briefs, pull-on diapers, training pants, feminine hygiene garments, and the like, which may provide some or all of the benefits of ease of application and removal including, in particular, easy insertion of the legs into the leg openings, sustained dynamic fit, prevention of leakage, sustained wearer comfort, and desirable appearance. Such an absorbent article is intended to be fit about a wearer's body to contain excreta and/or bodily exudates.

The absorbent article has a containment assembly having a front waist region, a back waist region opposed to the front waist region, a crotch region disposed between the front waist region and the back waist region, a front end edge, a back end edge, opposed side edges, a topsheet, a backsheet, and an absorbent core disposed at least partially between the topsheet and the backsheet. When the absorbent article is closed for wearing, portions of the side edges generally adjacent the front and back end edges are fastened or joined together, the remaining portions of the side edges define two leg openings, and the front end edge and the back end edge define a waist opening. The margins of the leg openings of the absorbent article have an elastic extensibility of at least about 50%.

The absorbent article may also have, at the margin of each leg opening, at least one outer leg cuff. The outer leg cuff and the adjacent materials may be mechanically incrementally stretched to provide a large amount of elastic extensibility as well as differential extensibility. The outer leg cuff may be folded or wrapped over the side edges of the materials defining the leg openings.

The absorbent article may thus provide ease of application and removal, sustained dynamic fit, prevention of leakage, sustained wearer comfort, and desirable appearance.

BRIEF DESCRIPTION OF THE DRAWINGS

While the specification concludes with claims particularly pointing out and distinctly claiming the subject matter which is regarded as forming the present invention, it is believed that the invention will be understood from the following description which is provided in conjunction with the accompanying drawings, in which like designations are used to designate substantially identical elements, and in which:

DETAILED DESCRIPTION OF THE INVENTION

The term "absorbent article" herein refers to a device which absorbs and contains excreta and/or bodily exudates and, more specifically, refers to a device which is placed against or in proximity to the body of the wearer to absorb and contain the excreta and/or exudates discharged from the body. The present invention is applicable to absorbent articles such as diapers, pull-on diapers, training pants, incontinence briefs, incontinence undergarments, absorbent inserts, diaper holders and liners, feminine hygiene garments, and the like.

Figure 1:
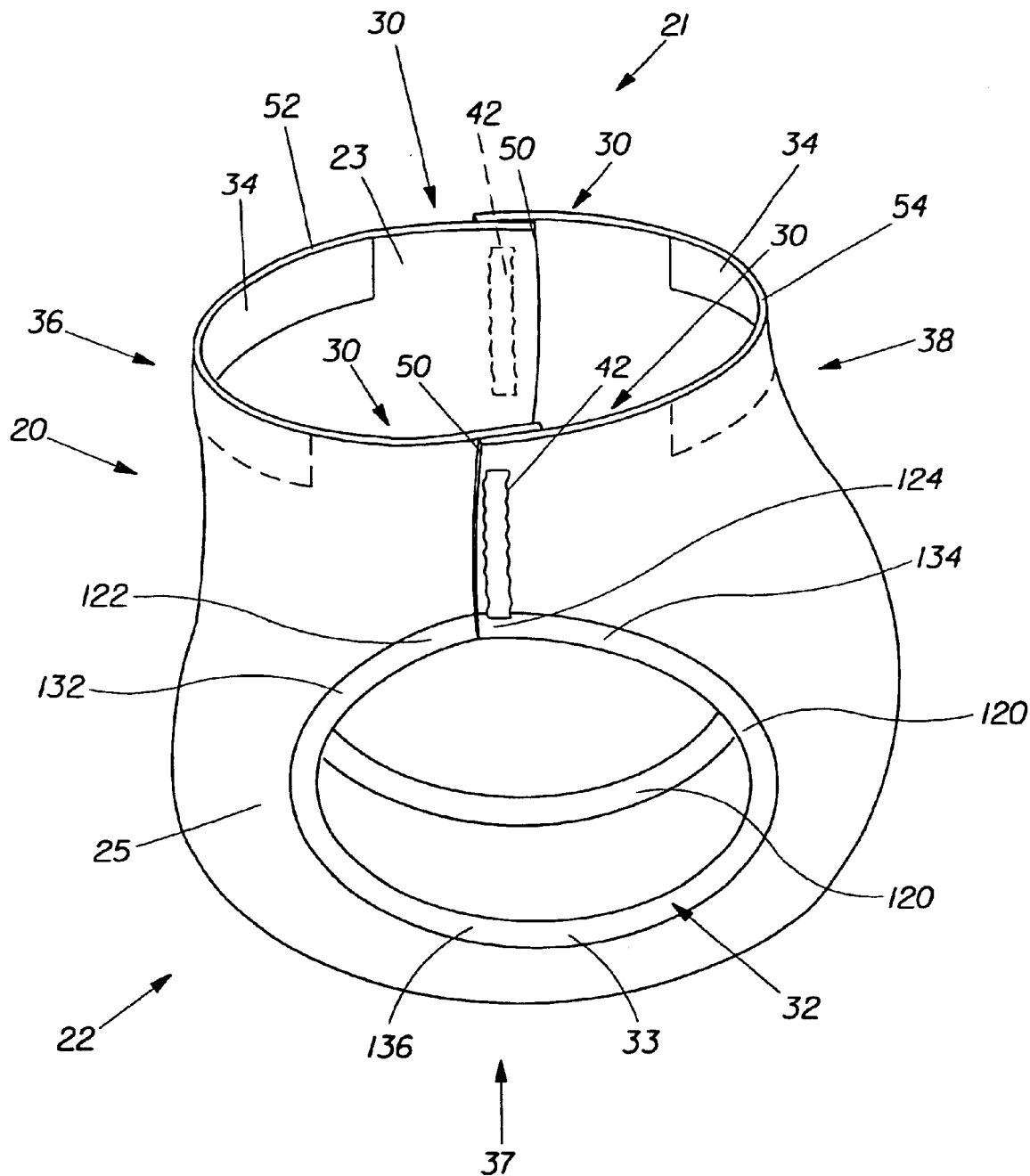
FIG. 1 is a side perspective view of a pre-closed absorbent article embodiment of the present invention.

An exemplary embodiment of an absorbent article of the present invention is the diaper 20, shown in FIG. 1 in pre-closed form suitable for use as a pull-on diaper or training pant. The diaper 20 preferably includes a containment assembly 22 and a waist feature 34. The diaper 20 has a front waist region 36, a back waist region 38 opposed to the front waist region 36, and a crotch region 37 located between the front waist region 36 and the back waist region 38. The periphery of the diaper 20 is defined by the outer edges of the diaper 20 in which side edges 50 lie generally parallel to the longitudinal centerline 100 and the front end edge 52 and back end edge 54 lie generally parallel to the lateral centerline 110 of the diaper 20. When the diaper 20 is closed for wearing, portions of the side edges 50 generally adjacent the front end edge 52 and back end edge 54 are fastened or joined together. In this closed state, the remaining portions of the side edges 50 define the edges 34 of two leg openings 32, and the front end edge 52 and the back end edge 54 define a waist opening 21.

The containment assembly 22 of the diaper 20 preferably includes a liquid pervious topsheet 24, a liquid impervious backsheet 26, and an absorbent core 28 which is preferably positioned between at least a portion of the topsheet 24 and the backsheet 26. The containment assembly 22 constitutes the main structure of the diaper 20 with other features added to form the composite diaper structure. Exemplary containment assembly structures are described in U.S. Pat. No. 5,899,895 issued to Robles et al. on May 4, 1999, U.S. Pat. No. 6,120,487 issued to Ashton on Sep. 19, 2000, and U.S. Pat. No. 5,151,092 issued to Buell et al. on Sep. 29, 1992, all of which are hereby incorporated herein by reference.

The backsheet 26 is generally that portion of the diaper 20 which is disposed adjacent the garment-facing surface 45 of the absorbent core 28 and which prevents the excreta and/or exudates contained therein from soiling articles which may contact the diaper 20, such as bedsheets and undergarments. The term "disposed" refers herein to the arrangement of an element in a particular physical relationship to other elements of the diaper 20. The backsheet 26 may be manufactured from a wide range of materials known in the art.

The backsheet 26 may be joined to the topsheet 24, the absorbent core 28 or any other element of the diaper 20 by any attachment means known in the art. The term "joined" refers herein to the attachment together of elements of the diaper 20, either by direct affixment of a first element to a second element or by affixment of the first element to an intermediate element which is affixed to the second element. The attachment means may include any suitable attachment means or combinations of attachment means known in the art.

The topsheet 24 is preferably disposed adjacent the body-facing surface 47 of the absorbent core 28 and may be joined to the absorbent core 28 and/or to the backsheet 26 by any attachment means known in the art. The topsheet 24 is preferably compliant, soft-feeling, and non-irritating to the wearer's skin. A suitable topsheet 24 may be manufactured from a wide range of materials known in the art.

The absorbent core 28 may comprise any absorbent material which is generally compressible, conformable, non-irritating to the wearer's skin, and capable of absorbing and retaining liquids such as urine and other bodily exudates. The absorbent core 28 may be manufactured in a wide variety of sizes and shapes, for example, rectangular, hourglass, "T"-shaped, asymmetric, etc. The absorbent core 28 may include any of a wide variety of liquid-absorbent materials commonly used in disposable diapers and other absorbent articles.

The diaper 20 may include at least one waist feature 34 as shown, for example, in FIG. 1 and other figures. The waist feature 34 may be elastically extensible to dynamically fit at the wearer's waist. The terms "elastic" and "elastically extensible" refer herein to the property of a material and/or an element of the diaper 20 whereby the material and/or the element can be elongated to a practical extent upon the application of tension and will substantially return to its original length or near its original length after the tension is released.

Figure 2:
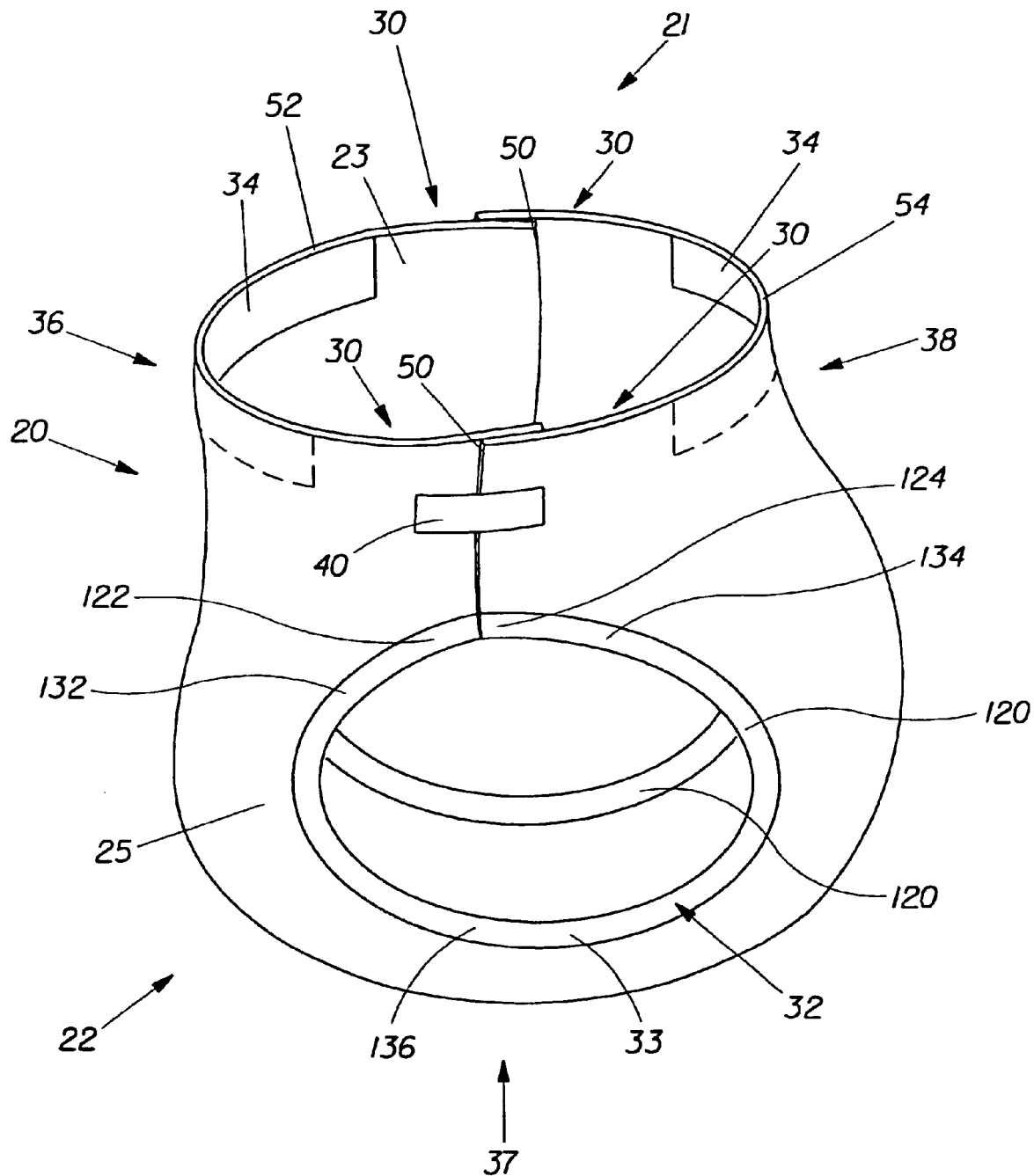
FIG. 2 is a side perspective view of an alternative absorbent article embodiment of the present invention in closed form.
Figure 3:
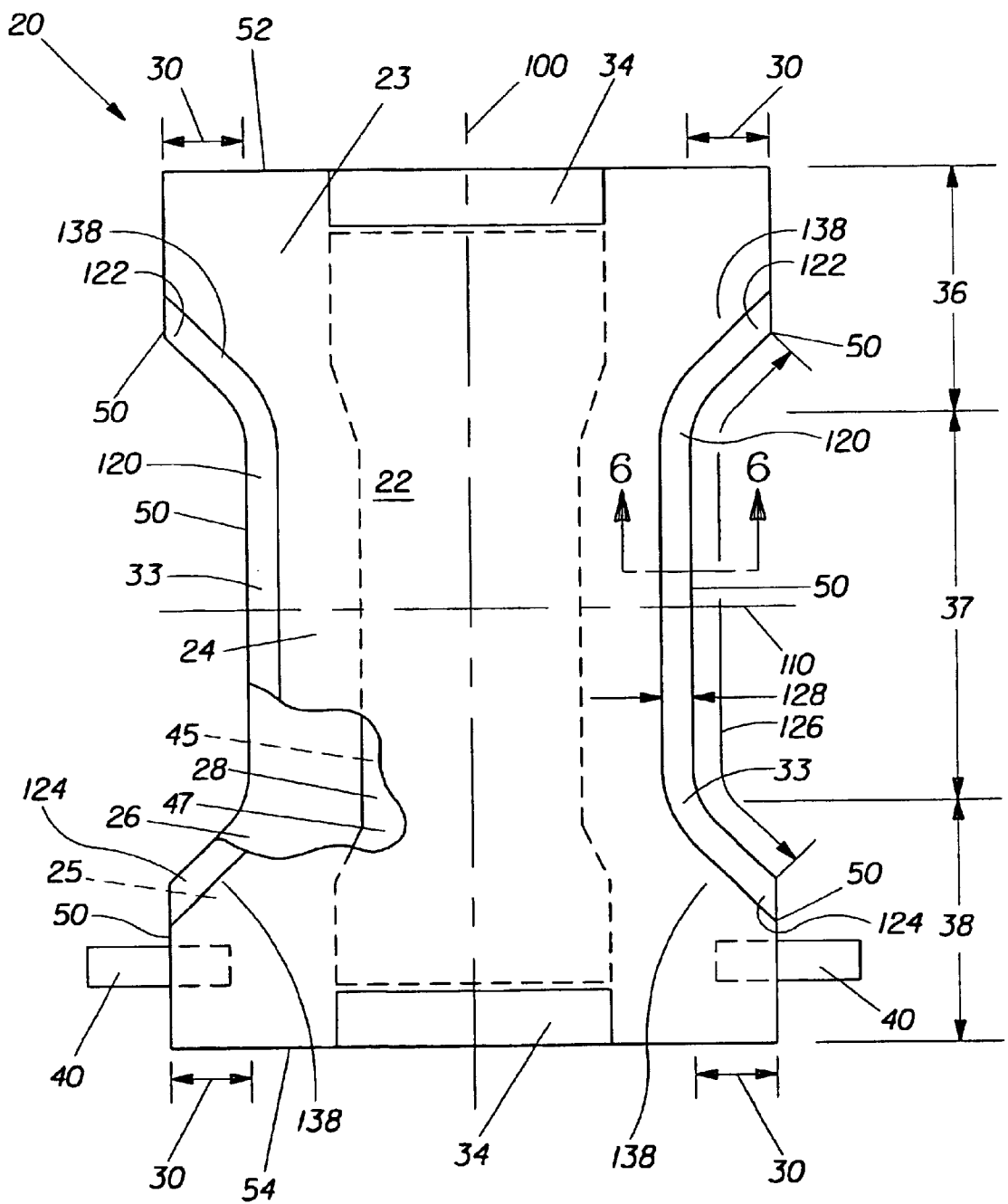
FIG. 3 is a simplified plan view of the absorbent article in FIG. 2, laid out flat with the inner surface facing the viewer, showing various sections and structural elements and having portions cut away to reveal underlying structure.
Figure 4:
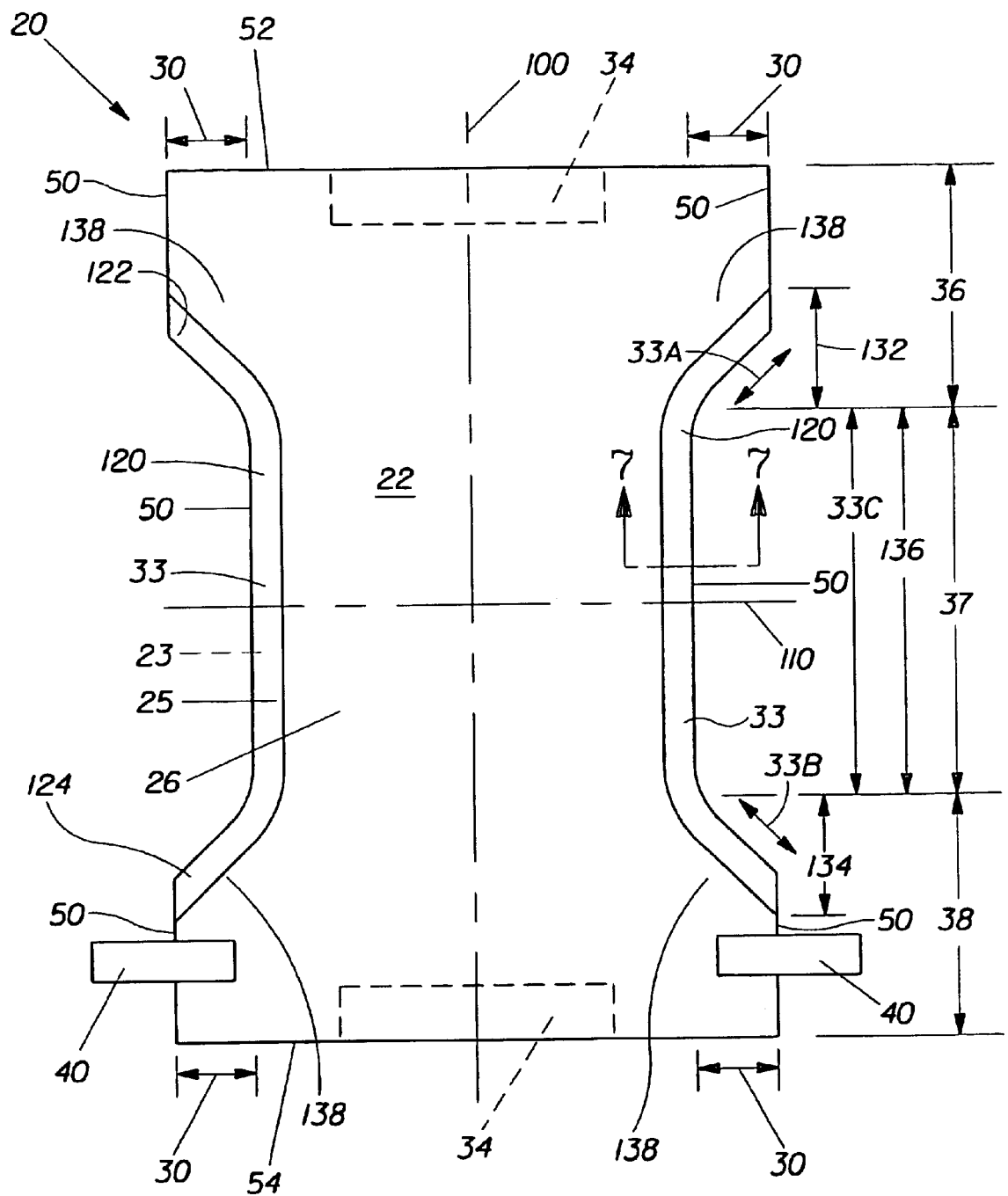
FIG. 4 is a simplified plan view of the article in FIG. 2, laid out flat with the outer surface facing the viewer and showing various sections and structural elements.

In some embodiments, the diaper 20 may include a fastening system 40 as shown, for example, in FIG. 2 and other figures. In general, the fastening system 40 may comprise any known fastening means. In some embodiments, the fastening system 40 may include refastenable fastening means that allow the diaper 20 to be opened and re-fastened, for ease of fitting on and removal from the body of the wearer and for adjustment while the diaper 20 is worn.

In some embodiments, the diaper 20 may be provided in a pre-closed form as shown, for example, in FIG. 1, suitable for use as a pull-on diaper, training pant, or the like. The term "closed" refers herein to a form of an article in which the article is assembled as when it is in use. The term "pre-closed" refers herein to an article provided to the user in closed form. The pre-closed diaper 20 may have its opposing side edges 50 in the front waist region 36 and the back waist region 38 joined by seams or welds 42, as shown in FIG. 1. The seams or welds 42 may be bonded by any suitable bonding means known in the art which is appropriate for the specific materials employed. A pre-closed diaper 20 may alternatively have its opposing side edges 50 fastened together by any suitable fastening means, including those described above for the fastening system 40 and shown in FIG. 2. In some embodiments, the fastening system 40 of a pre-closed diaper 20 may have refastenable fastening means that allow the diaper 20 to be opened and re-fastened, for ease of fitting on and removal from the body of the wearer and for adjustment while the diaper 20 is worn.

The diaper 20 may also include side panels 30 disposed in the back waist region 38, in the front waist region 36, or in both the front waist region 36 and the back waist region 38 as shown, for example, in FIG. 1 and other figures. The side panels 30 may be constructed in any suitable configuration known in the art. At least a portion of the side panels 30 may be elastically extensible, substantially inelastically extensible, or substantially inextensible.

The leg openings 32 of the diaper 20 have leg opening margins 33 having a high elastic extensibility. The term "margin" refers herein to the outside limit and adjoining surface of a portion or element of the diaper 20. The term "elastic extensibility" refers herein to the degree to which a material and/or an element of the diaper 20 can be elongated to a practical extent, relative to its relaxed length, and substantially return to its relaxed length or near its relaxed length after the elongating tension is released. The term "elastic extension" herein refers to the degree to which the material and/or element is elongated within its range of elastic extensibility, in the particular situation being described. The elastic extensibility and/or elastic extension can be expressed as a proportion of the relaxed length. When expressed as a proportion, as in "150 percent extension", for example, the value is the proportion of the relaxed length by which the material or element can be substantially elastically elongated. The terms "high elastic extensibility", "highly elastically extensible", and the like, refer herein to an elastic extensibility equal to or greater than about 60%. In some embodiments, the maximum elastic extensibility of an element of the diaper 20 may be about 300%.

For the present purpose, it is the effective elastic extensibility that is of interest. Therefore, references herein to embodiments in which an elastically extensible material or element may be constrained by other elements of the diaper 20 from expanding or contracting to the extent to which it could expand or contract in isolation refer to the constrained state. Also, descriptions herein of the elastic extensibility, the elastic extension, and the elastically extended dimensions of exemplary embodiments refer to the elastically extended state of the diaper 20 under the effect of a lateral spreading force having a magnitude of about 5 kg-force applied at or adjacent the uppermost distal points 146 of the margins 33 of the leg openings 32 of the closed diaper 20. The abbreviation "kg" is used herein for the kilogram unit of measurement. This 5 kg lateral spreading force represents the lateral spreading force applied in preparation for, and during, the application or donning of the diaper 20.

With reference to the leg opening margin 33, descriptions herein of its elastic extensibility refer particularly to the elastic expansion of its circumference. Thus, for example, the term "highly elastically extensible leg opening margin" refers herein to a leg opening margin 33 having an elastic extensibility such that its circumference, and thereby the circumference of the leg opening 32, may be elastically expanded by about 60% or greater under the effect of the 5 kg lateral spreading force described above.

The leg opening margin 33 may have differential properties. The term "differential" refers herein to that which relates to or constitutes a difference and the term "differential properties" refers herein to different values for a property in different portions of an element of the diaper 20. For example, the leg opening margin 33 may have differential elastic moduli, such as a first elastic modulus in a first portion 33A adjacent the front waist region 36 of the diaper 20 and a second elastic modulus in a second portion 33B adjacent the back waist region 38.

As another example of differential properties, in some embodiments, the leg opening margin 33 may be differentially elastically extensible, including having a first elastic extensibility in a first portion 33A adjacent the front waist region 36, a second elastic extensibility in a second portion 33B adjacent the back waist region 38, and a third elastic extensibility in a third portion 33C adjacent the crotch region 37. In some embodiments, the first elastic extensibility referenced above preferably is about 100% or greater and in some embodiments, this first elastic extensibility preferably is about 150% or greater. Similarly, in some embodiments, the second elastic extensibility preferably is about 80% or greater and in some embodiments, this second elastic extensibility preferably is about 120% or greater. In these exemplary embodiments, the third elastic extensibility may be less than either the first or the second elastic extensibility, because the crotch region 37 is generally a zone of lower motion than the front and rear waist regions. Thus, for example, in some embodiments, the third elastic extensibility preferably is about 30% or greater and in some embodiments, this third elastic extensibility preferably is about 50% or greater.

Figure 8:
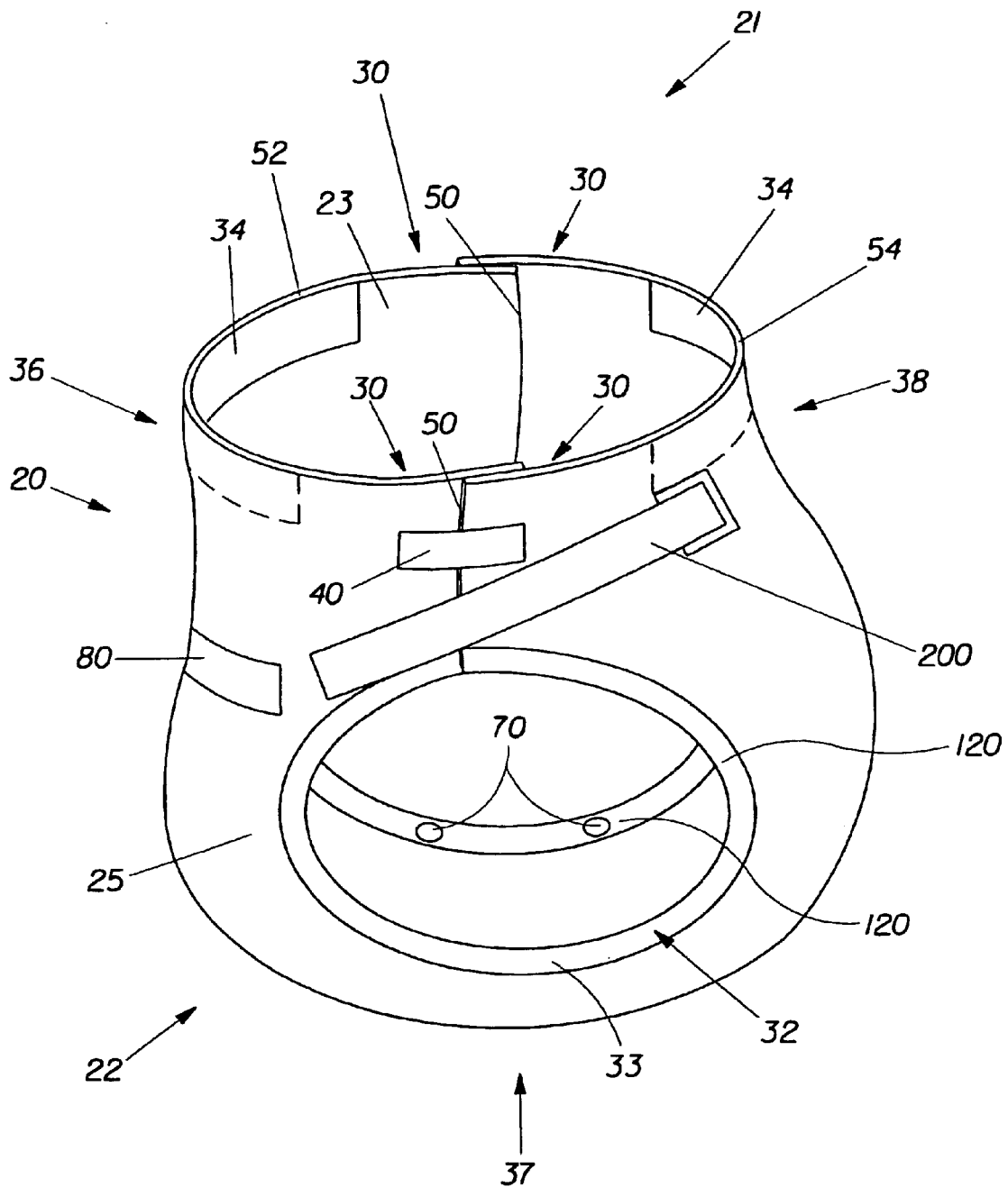
FIG. 8 is a side perspective view of an alternative absorbent article embodiment of the present invention.

Although the above examples refer to a leg opening margin 33 having differential properties in three portions, any number of portions of the leg opening margin 33 may have differential properties. For example, a leg opening margin 33 may have only two portions having differential properties, such as only a first portion 33A and a second portion 33B. Similarly, the leg opening margin 33 may have four or more portions having differential properties. As an example, a leg opening margin 33 may have the three portions having differential elastic extensibility described above and a fourth portion having at least one high friction retention zone 70 disposed at least partially on or adjacent the inner surface 23 of the containment assembly 22, as shown in FIG. 8, to resist movement of the diaper 20 relative to the surface of the wearer's body. Examples of a high friction retention zone 70 are described in co-pending and commonly assigned U.S. patent application Ser. No. 09/312,997 filed on May 17, 1999, which is hereby incorporated herein by reference. As another example, a leg opening margin 33 may have a portion having a differential elastic extensibility designed particularly to accommodate the elastic extension of an adjacent element of the diaper 20, such as an elastic side panel 30 or another element.

The leg opening margin 33 may comprise materials incrementally stretched by methods such as ring rolling between meshed corrugated rolls, stamping with meshing platens, and the like. Examples of incremental stretching methods and suitable incrementally stretched materials are described in commonly assigned U.S. Pat. No. 5,167,897 issued to Weber et al. on Dec. 1, 1992, which is hereby incorporated herein by reference.

An incrementally stretched laminate is formed with the non-elastomeric material in a substantially relaxed, i.e., non-stretched state. The laminate is then incrementally stretched, resulting in the non-elastomeric material being strained beyond its elastic limit and in the creation of plastically deformed areas of the non-elastomeric material, which areas generally remain laminated with the elastomeric material. In some embodiments, the laminate can be incrementally stretched to the elastic limit of the elastomeric material. In the finished incrementally stretched laminate in a relaxed state, the cumulative bulk of the non-elastomeric material may be substantially no more than that of the original laminate prior to its being incrementally stretched. Thus, both the maximum elastic extension and the elastic extensibility of an incrementally stretched laminate may be significantly greater than those of a conventionally gathered structure.

The diaper 20 of the present invention may also include at least one highly elastically extensible outer leg cuff 120. The term "leg cuff" refers herein to an element of a diaper 20 which has the function of forming a gasket around the leg of a wearer to prevent leakage. The term "outer leg cuff" refers herein to a leg cuff disposed substantially adjacent the portions of the side edges 50 defining the leg openings 32 when the diaper 20 is closed and distally relative to any other leg cuff element which may also be present in a diaper 20, such as an inner cuff, a barrier cuff, a containment flap, and the like.

The outer leg cuff 120 may be substantially straight or may have at least a portion which is curved. For example, in an embodiment in which the side edge 50 defining the leg opening 32 of the diaper 20 is substantially straight, the outer leg cuff 120 may also be substantially straight. In embodiments in which the side edge 50 defining the leg opening 32 is curved over at least a portion of its length 126, the outer leg cuff 120 may be curved to substantially conform to the curve of the side edge 50. In some embodiments, the outer leg cuff 120 may have straight segments arranged substantially end to end to form at least a portion of a curve and/or to substantially conform to the curve of the side edge 50.

The outer leg cuff 120 has a first end 122 and a second end 124. The first end 122 preferably is disposed in the upper front quadrant of the circumference of the leg opening 32 edge when the diaper 20 is closed. The second end 124 preferably is disposed in the upper back quadrant of the circumference of the leg opening 32 edge when the diaper 20 is closed. The term "upward" refers herein to a direction generally from the feet toward the head on the body of a wearer in all bodily positions and postures. Consistent with this definition, the term "upper" refers herein to a location or relative position generally farther upward than another location or relative position with which it is contrasted. The terms "downward" and "lower" refer herein to generally opposite directions and locations or relative positions from those corresponding to "upward" and "upper", respectively. Thus, for example, the quadrants of the circumference of a leg opening 32 edge may be characterized as upper and lower and front and back, based on their relative locations and on their proximity to the front and back waist regions, 36 and 38, respectively.

In some preferred embodiments, the first end 122 and the second end 124 of the outer leg cuff 120 may be disposed adjacent the transition points between the portions of the side edges 50 which are fastened or joined together to close the diaper 20 and the portions of the side edges 50 defining the leg openings 32. In such an embodiment, as can be seen in FIG. 1, the first end 122 and the second end 124 may be disposed adjacent each other when the diaper 20 is closed and the outer leg cuff 120 may thus substantially encircle the leg opening 32. In some preferred embodiments, the first end 122 and second end 124 may be joined together to completely encircle the leg opening 32. For example, in an embodiment of a pre-closed diaper 20, in which the opposing side edges 50 in the front waist region 36 and the back waist region 38 are joined by seams or welds 42, the first end 122 and second end 124 may extend into the area of the seams or welds 42 and thus be joined to form a completely encircling outer leg cuff 120.

The outer leg cuff 120 may be disposed at least partially interiorly to the formed diaper 20 adjacent the inner surface 23 of the containment assembly 22. Alternatively, the outer leg cuff 120 may be disposed at least partially exteriorly to the formed diaper 20 adjacent the outer surface 25 of the containment assembly 22. Also, the outer leg cuff 120 may be disposed both interiorly and exteriorly as, for example, in an embodiment in which it is wrapped over the side edges 50 of the materials defining the leg openings 32.

The outer leg cuff 120 has a length 126, which is measured along its surface between its first end 122 and second end 124. The outer leg cuff length 126 when the diaper 20 is laid out flat may be of any magnitude less than the total length of the adjacent side edge 50, measured along the contour of the side edge 50 between the front end edge and the back end edge. In some embodiments, the length 126 when the diaper 20 is closed preferably is about equal to the circumference of the leg opening 32 as defined by the side edge 50. In some embodiments, the length 126 preferably is about 5 mm to 20 mm greater than the circumference of the leg opening 32. For example, in such an embodiment, the ends of the outer leg cuff 120 may be overlapped and joined to completely encircle the leg opening 32.

The outer leg cuff 120 also has a width 128, which is measured substantially perpendicularly to its length direction. The outer leg cuff width 128 may be of any magnitude suitable for fitting around the leg. In some embodiments, the outer leg cuff 120 preferably has a width 128 of about 10 mm or greater and in some embodiments, the width 128 preferably is about 16 mm or greater. The abbreviation "mm" is used herein for the millimeter unit of measurement. Also, in some embodiments, the outer leg cuff 120 preferably has a width 128 of about 60 mm or smaller and in some embodiments, the width 128 preferably is about 30 mm or smaller. It has been found that an outer leg cuff width 128 of about 20 mm is suitable over a wide range of sizes of wearers and of the diaper 20.

The outer leg cuff 120 may be joined to the backsheet 26, the topsheet 24, to both the backsheet 26 and the topsheet 24, and/or to any other element of the diaper 20 by any attachment means known in the art which is suitable for the materials involved. For example, the attachment means may include any of those listed above in reference to the backsheet 26. The outer leg cuff 120 preferably is joined over at least the majority of at least one of its surfaces to another element of the diaper 20, such that only a minor edge or flap of the outer leg cuff 120 remains substantially free. In some embodiments, the outer leg cuff 120 preferably is joined over substantially the entirety of at least one of its surfaces to another element of the diaper 20, such that only a minimal edge or flap of the outer leg cuff 120 remains substantially free. For example, in some embodiments, the width of the free edge or flap may be about 5 mm or less, in some embodiments, the free width may be about 2 mm or less and, in some embodiments, the free width may be about 1 mm or less. The practical minimum width of the free edge or flap may be about 0.01 mm.

In some embodiments, at least a portion of the outer leg cuff 120 may be joined to itself, as for example when the outer leg cuff 120 is wrapped over the side edges 50 defining the leg openings 32. In such an embodiment in which, for example, an adhesive is used to join the outer leg cuff 120 to another element or elements of the diaper 20, the adhesive may also join exposed portions of the inner folded surface of the outer leg cuff 120 to itself. In other embodiments, the outer leg cuff 120 may be joined only to another element or elements of the diaper 20 and not to itself, except at the first end 122 and second end 124 in some embodiments, as described above. For example, the outer leg cuff 120 may be wrapped over the side edges 50 such that its inner folded surface is not joined to itself.

In some embodiments, the outer leg cuff 120 may be discrete. The term "discrete" refers herein to an element of the diaper 20 which is formed separately and distinctly from any other element and is joined to another element or elements of the diaper 20, every component of the discrete element being wholly contained within the discrete element and no component of the discrete element being continuous with an element outside the discrete element. For example, a leg cuff formed of a portion of a continuous topsheet is not discrete, while a leg cuff formed of separate and distinct pieces and joined to a topsheet may be discrete. As another example, a composite structure including both an outer leg cuff and an inner leg cuff or a containment flap is not a discrete outer leg cuff.

Figure 6:
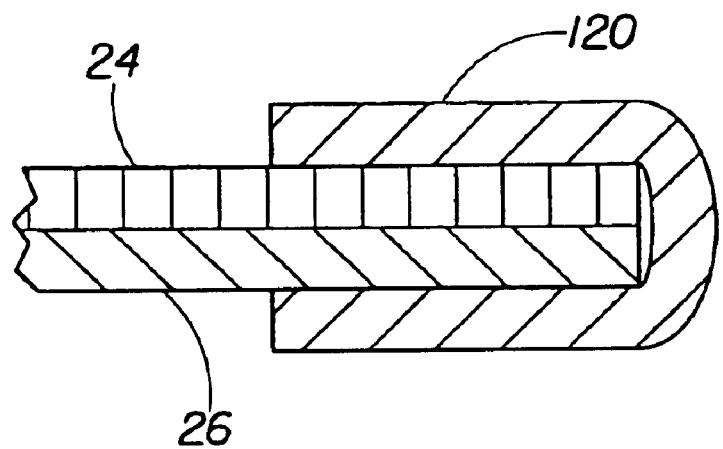
FIG. 6 is a partial cross-sectional view of an absorbent article embodiment of the present invention, showing various structural elements, taken along section line 6—6 of FIG. 3.
Figure 7:
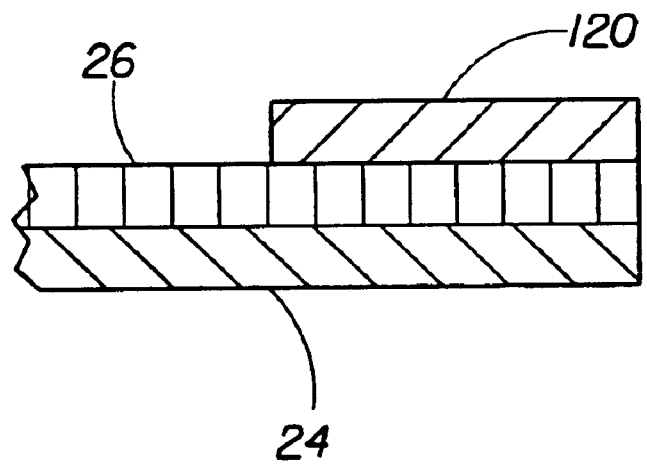
FIG. 7 is a partial cross-sectional view of an alternative embodiment of the absorbent article of the present invention, showing various structural elements, taken along section line 7—7 of FIG. 4.

In some embodiments, the outer leg cuff 120 is wrapped over the side edges 50 of the materials defining the leg openings 32, as shown in FIG. 6. In such embodiments, a portion of the outer leg cuff width 128 is disposed interiorly and a portion is disposed exteriorly to the formed diaper 20. Although the embodiments shown in the Figures and described herein, in which the outer leg cuff 120 is wrapped over the side edges 50, generally have substantially equal portions of the outer leg cuff width 128 disposed interiorly and exteriorly, the outer leg cuff 120 may be folded asymmetrically for wrapping over the side edges 50. Thus, for example, any distribution of the outer leg cuff width 128 in the range from its being disposed entirely exteriorly as shown in FIG. 7, through its being disposed equally interiorly and exteriorly, to its being disposed entirely interiorly, may be selected for a particular embodiment.

A wrapped embodiment of an outer leg cuff 120 may provide a finished appearance to at least a portion of the circumference of the leg opening 32. By covering the cut edges of the materials over which it is wrapped, such a wrapped cuff may visually mask discontinuities, such as those at a transition from a side panel 30 to an element of the containment assembly 22. Thus, a wrapped outer leg cuff 120 may form a homogeneous surface and thus create a homogeneous appearance around at least a portion of the circumference of the leg opening 32.

The outer leg cuff 120 may comprise any material known in the art which is suitable for the purposes and functions described herein. The material of the outer leg cuff 120 preferably is compliant, soft-feeling, and nonirritating to the skin such that it has minimal negative effect on the wearer's comfort and/or the visual and/or tactile perception of the user. Suitable materials for use in the construction of the outer leg cuff 120 include, but are not limited to, materials used in other elements of the diaper 20, such as topsheet 24 material, backsheet 26 material, waist feature 34 material, side panel 30 material, elastic strip material, and the like. The outer leg cuff 120 may comprise a single layer or a laminate of suitable materials. Such a laminate may include, for example, nonwoven material, film, formed film, scrim material, foam, and/or strip material. The orientation of such a laminate in an outer leg cuff 120 may dispose any of the included materials toward the skin of the wearer. For example, a non-woven material may be disposed to face the skin or a film may be so disposed. In some embodiments, the outer leg cuff 120 may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801 entitled "Web Materials Exhibiting Elastic-Like Behavior" issued to Chappell et al. on May 21, 1996, which is hereby incorporated herein by reference.

The outer leg cuff 120 may also have differential properties. For example, the outer leg cuff 120 may have differential elastic moduli, such as a first elastic modulus in a first portion 132 adjacent the front waist region 36 of the diaper 20 and a second elastic modulus in a second portion 134 adjacent the back waist region 38. In some embodiments, the outer leg cuff 120 may have differential properties corresponding to the presence or absence of one or more components of the laminate structure in different portions. For example, in an outer leg cuff 120 having a laminate structure including an elastic film material, the film may be present in some portions and not present in other portions. Such differential properties may also include the thickness, width, material composition, and/or some other property.

In some embodiments, the outer leg cuff 120 may have substantially uniform properties throughout its area when it is formed, but may have differential properties when incorporated into the diaper 20. For example, the outer leg cuff 120 may be elastically pre-extended in at least one portion and substantially relaxed in at least one other portion when it is joined to the containment assembly 22. In various embodiments, the proportion of the outer leg cuff 120 which may be elastically pre-extended when it is joined to the containment assembly 22 may range from none to substantially the entirety of the outer leg cuff 120.

As an example of differential properties, in some embodiments, the outer leg cuff 120 may be differentially elastically extensible, including having a first elastic extensibility in a first portion 132 adjacent the front waist region 36, a second elastic extensibility in a second portion 134 adjacent the back waist region 38, and a third elastic extensibility in a third portion 136 adjacent the crotch region 37. In some embodiments, the first elastic extensibility referenced above preferably is about 100% or greater and in some embodiments, this first elastic extensibility preferably is about 150% or greater. Similarly, in some embodiments, the second elastic extensibility preferably is about 80% or greater and in some embodiments, this second elastic extensibility preferably is about 120% or greater. In these exemplary embodiments, the third elastic extensibility may be less than either the first or the second elastic extensibility, because the crotch region 37 is generally a zone of lower motion than the front and rear waist regions. Thus, for example, in some embodiments, the third elastic extensibility preferably is about 30% or greater and in some embodiments, this third elastic extensibility preferably is about 50% or greater.

Although the above examples refer to an outer leg cuff 120 having differential properties in three portions, any number of portions of the outer leg cuff 120 may have differential properties. For example, an outer leg cuff 120 may have only two portions having differential properties, such as only a front portion and a rear portion. Similarly, the outer leg cuff 120 may have four or more portions having differential properties. As an example, an outer leg cuff 120 may have the three portions having differential ranges of elastic extensibility described above and a fourth portion having at least one high friction retention zone 70 disposed at least partially on or adjacent the inner surface 23 of the containment assembly 22, as shown in FIG. 8, to resist movement of the diaper 20 relative to the surface of the wearer's body. As another example, an outer leg cuff 120 may have a portion having a differential elastic extensibility designed particularly to accommodate the elastic extension of an adjacent element of the diaper 20, such as an elastic side panel 30 or another element.

The outer leg cuff 120 may comprise a laminate of materials incrementally stretched by methods such as ring rolling between meshed corrugated rolls, stamping with meshing platens, and the like. In some embodiments of the diaper 20, not only the outer leg cuff 120 may be incrementally stretched but, in addition, at least a portion 138 of the materials defining the leg opening 32 and the materials adjacent the leg opening 32 and the outer leg cuff 120 may also be incrementally stretched. For example, a laminate form of an outer leg cuff 120 may be separately incrementally stretched prior to being joined to another element of the diaper 20 and then at least a portion 138 of the area of the diaper 20 at or adjacent the leg opening 32 may be incrementally stretched. Thus, in such an embodiment, at least a portion of the outer leg cuff 120 may be incrementally stretched at least twice.

In other embodiments, a laminate form of an outer leg cuff 120 may be joined to another element of the diaper 20 prior to being incrementally stretched. At least a portion of the outer leg cuff 120 may then be incrementally stretched simultaneously with a portion 138 of the adjacent materials. Thus, various combinations of elastic pre-extension of the outer leg cuff 120, incremental stretching of the outer leg cuff 120, and incremental stretching of the materials of the containment assembly 22 adjacent the outer leg cuff 120 may be utilized in order to provide particular ranges of effective elastic extensibility in particular areas of the diaper 20.

Such embodiments in which at least a portion of the outer leg cuff 120 and the adjacent material or materials are incrementally stretched may have desirable elastic extensibility properties. For example, because the adjacent material is also incrementally stretched, the circumference of the leg opening 32 may be elastically extensible throughout the full range of elastic extensibility of the outer leg cuff 120, itself. Also, because the adjacent material has been incrementally stretched, rather than being gathered, its cumulative bulk in the relaxed state may be substantially no more than that of the material prior to its being incrementally stretched. Thus, while the adjacent material may be extensible during the application of the diaper 20 onto the body of the wearer, it may not "balloon" or "blouse" away from the bodily contours during the period of wear. Furthermore, materials or elements may be incrementally stretched to different degrees in different areas and thus may have desirable differential properties, as described above.

The advantages of incrementally stretched materials with respect to elastic extensibility may be applied in the designs of diapers which are significantly easier to apply onto the body of a wearer and/or are easier for a wearer to don, in comparison to diapers having conventional gathered outer leg cuffs. For example, in some embodiments of the present invention, the relaxed circumference of the leg opening margin 33 preferably is smaller than the lower end of a range of leg circumferences of wearers for whom the diaper 20 is designed. In the same embodiments, the elastically extended circumference of the leg opening margin 33 preferably is significantly larger than the upper end of the range of leg circumferences of the intended wearers. The relationship of the relaxed leg opening margin 33 circumference to the smallest leg circumference helps to ensure that the outer leg cuff 120 will contract around the leg and perform its intended function as a gasket to prevent leakage. The benefit of the elastically extended leg opening margin 33 circumference being significantly larger than the largest leg circumference is that the diaper 20 can be applied or donned easily. For example, in some of these embodiments, the elastically extended circumference of the leg opening margin 33 preferably is at least about 20% larger than the upper end of the range of leg circumferences of the intended wearers and, in some embodiments, it preferably is at least about 50% larger than the upper end of the range of leg circumferences of the intended wearers. For instance, the feet of an active wearer and even shoed feet can relatively easily be inserted into leg openings 32 that are 50% larger than the leg circumference.

In addition, when the diaper 20 is expanded laterally in preparation for, and during the application or donning of the diaper 20, an important resultant effect is that the orientation of the leg opening 32 having such a highly elastically extensible leg opening margin 33 is rotated away from a longitudinal orientation and toward a lateral orientation. Since the insertion of a wearer's feet and legs is constrained by the anatomy to a direction generally parallel to the longitudinal direction, the orientation of the leg opening 32 generally perpendicular to this direction of insertion makes the insertion easier. The orientation of the leg opening 32 is rotated because the direction of spreading of the diaper 20 is lateral and, thus, the uppermost distal point on the edge of the leg opening margin 33 is displaced laterally outwardly, i.e., more distally, when the leg opening margin 33 is elastically expanded.

As an aid for understanding, an exemplary pant embodiment of the diaper 20 having outer leg cuffs 120 may be described as follows. The outer leg cuffs 120 may comprise an incrementally stretched laminate formed of a single layer of an elastomeric film, such as 2.0 mil (approximately 0.05 mm) thick BEX501 film available from Tredegar Industries, Inc. of Terre Haute, Ind., U.S.A., sandwiched between two layers of a polypropylene spun-bonded non-woven material, such as P-10 non-woven available from BP Amoco. The elastomeric film may be elastically extended to about 125% elastic extension for lamination with the relaxed layers of non-woven material. Thus, the non-woven material layers of the outer leg cuff 120 may be gathered by the elastomeric film when it is allowed to relax. The laminated materials may be thermally bonded together to form the outer leg cuff 120.

At the time of joining the outer leg cuff 120 to the containment assembly 22, the crotch portion 136 of the outer leg cuff 120 may be elastically extended to about 125%, while the remainder of the outer leg cuff 120 may be joined to the containment assembly 22 in a substantially relaxed state. Upon being allowed to relax, the crotch portion 136 of the outer leg cuff 120 thus may contract and gather the materials of the crotch region 37 of the containment assembly 22, forming a cup or bucket adjacent the absorbent core 28 in the crotch region 37.

As described above, areas of the diaper 20 adjacent the outer leg cuff 120 may be incrementally stretched. For example, the portion 132 of the outer leg cuff 120 adjacent the front waist region 36, and the area of the containment assembly 22 to which this portion 132 of the outer leg cuff 120 is joined, may be incrementally stretched after the outer leg cuff 120 is joined to the containment assembly 22. This incremental stretching of the joined outer leg cuff 120 and the adjacent material may yield the desired ranges of elastic extensibility.

Figure 5:
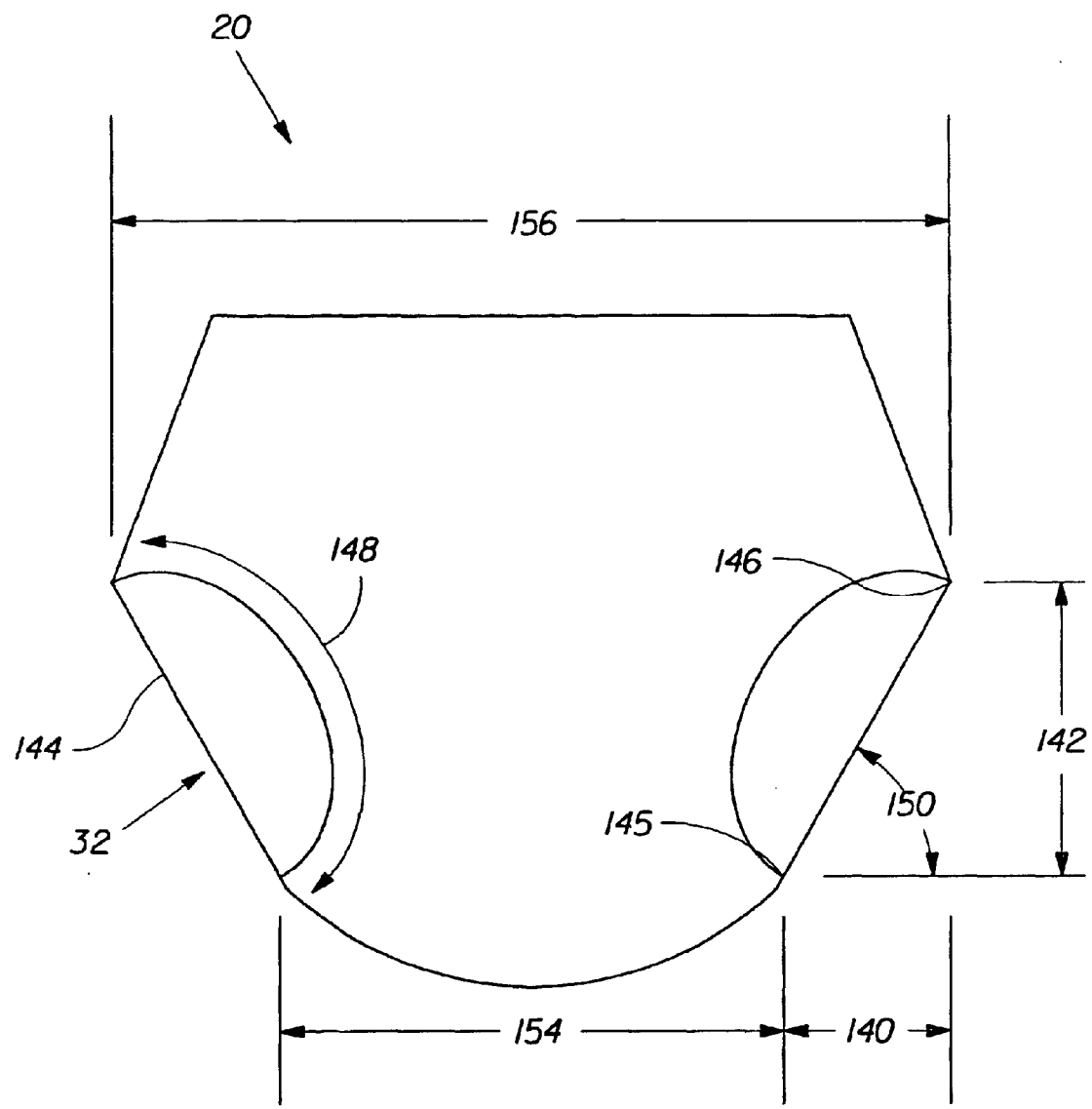
FIG. 5 is a plan view of an assembled absorbent article embodiment of the present invention, laid out flat with the front portion facing the viewer, showing various extensible elements and defined dimensions.

The following terms and dimensions may be defined in reference to the depiction in FIG. 5 of a diaper 20 closed and laid flat for measurement purposes:

a) the terms "flat lateral width" and "flat longitudinal height" refer herein to dimensions measured substantially parallel to the lateral centerline 110 and longitudinal centerline 100, respectively, of the diaper 20;

b) the lowermost proximal point 145 and uppermost distal point 146 are points on the leg opening margin 33 where the margin 33 contacts the leg of the wearer and forms a gasket around the leg when the diaper 20 is worn, excluding any loose flap of material which remains generally free to fold or bend away from the leg, if any such loose flap is present in the diaper being measured;

c) the diagonal axis 144 of the leg opening is defined by the lowermost proximal point 145 of the leg opening margin 33 and the uppermost distal point 146 of the leg opening margin 33;

d) the flat lateral width 140 of the leg opening 32 is the lateral distance from the lowermost proximal point 145 of the leg opening margin 33 to the uppermost distal point 146 of the leg opening margin 33, i.e., the lateral component of the vector length of the diagonal axis 144;

e) the flat longitudinal height 142 of the leg opening 32 is the longitudinal distance from the lowermost proximal point 145 of the leg opening margin 33 to the uppermost distal point 146 of the leg opening margin 33, i.e., the longitudinal component of the vector length of the diagonal axis 144;

f) the flat lateral width 154 of the crotch region 37 is the lateral distance from the lowermost proximal point 145 of one leg opening margin 33 to the lowermost proximal point 145 of the opposing leg opening margin 33;

g) the overall flat lateral width 156 of the diaper 20 is the lateral distance from the uppermost distal point 146 of one leg opening margin 33 to the uppermost distal point 146 of the opposing leg opening margin 33, i.e., the sum of the crotch region flat lateral width 154 and twice the leg opening flat lateral width 140;

h) the arc length 148 of the arcuate front portion of the leg opening 32 is the length of one quadrant of an ellipse having axes respectively equal to twice the leg opening flat lateral width 140 and twice the leg opening flat longitudinal height 142; and i) the orientation angle 150 of the leg opening 32 is defined by the lateral centerline 110 and the diagonal axis 144 of the leg opening 32 and its tangent is the ratio between the flat longitudinal height 142 and the flat lateral width 140 of the leg opening 32.

With this exemplary diaper 20 closed and laid flat in a relaxed state, each leg opening 32 may have a flat lateral width 140 of about 59 mm and a flat longitudinal height 142 of about 80 mm. The crotch region 37 relaxed flat lateral width 154 may be about 100 mm. Also, the overall relaxed flat lateral width 156 of the diaper 20 may be about 218 mm. The diagonal axis 144 of the leg opening 32 in the relaxed state may thus have a length of about 99 mm. The back portion of the leg opening margin 33 may describe a substantially straight line and may lie generally along the diagonal axis 144. In this embodiment, the front portion of the leg opening margin 33 may describe an arcuate shape when laid flat. This arcuate shape may be generally concave downward, i.e., the arc may lie upward on the diaper 20, relative to the back portion of the leg opening margin 33 and relative to the diagonal axis 144. The relaxed arc length 148 of the leg opening 32 may be about 110 mm in the relaxed state.

Thus, in this embodiment, the circumference of the relaxed leg opening margin 33 may be about 209 mm, which is the sum of the relaxed diagonal axis 144 length and the relaxed arc length 148. Also, the orientation angle 150 of the leg opening 32 in this embodiment in the relaxed state may thus be about 54 degrees. The ease of application and specifically the ease of inserting the wearer's leg into the leg opening 32 is generally inversely proportional to the magnitude of the orientation angle 150. The optimal orientation angle 150 would be approximately zero degrees, i.e., when the leg opening margin 33 is generally parallel to the lateral axis and generally perpendicular to the longitudinal axis of the diaper 20.

Under the effect of the 5 kg spreading force described above, the flat lateral width 140 of each leg opening 32 of the above exemplary embodiment may expand to about 149 mm, while the flat longitudinal height 142 of the leg opening 32 may remain substantially unchanged at about 80 mm. The crotch region 37 relaxed flat lateral width 154 may also remain substantially unchanged at about 100 mm. The overall flat lateral width 156 of the elastically extended diaper 20 may be about 398 mm. Thus, the diagonal axis 144 length of the leg opening 32 may expand to about 169 mm and the arc length 148 of the leg opening 32 may expand to about 184 mm.

Therefore, under the effect of the 5 kg spreading force, the circumference of the elastically extended leg opening margin 33 of the exemplary diaper 20 may be about 353 mm and the elastic extensibility of the leg opening margin 33 may be about 69%. In some embodiments, the elastic extensibility of the leg opening margin 33 under the effect of the 5 kg spreading force preferably is about 60% or greater and, in some embodiments, the elastic extensibility of the leg opening margin 33 under the effect of the 5 kg spreading force preferably is about 65% or greater.

The orientation angle 150 in this exemplary embodiment may thus decrease to about 28 degrees, i.e., the leg opening margin 33 may be rotated about 25 degrees toward the lateral direction, under the effect of the 5 kg spreading force. In some embodiments, the orientation angle 150 under the effect of the 5 kg spreading force preferably is about 30 degrees or less and, in some embodiments, the orientation angle 150 under the effect of the 5 kg spreading force under the effect of the 5 kg spreading force preferably is about 28 degrees or less.

Also, the overall flat lateral elastic extensibility of the diaper 20 may be about 83%. In addition, the crotch region 37 flat lateral width 154 may be about 25% of the overall flat lateral width 156 of the elastically extended exemplary diaper 20.

This exemplary diaper 20 may be suitable for use by wearers having leg circumferences ranging from about 232 mm to about 294 mm. This determination is based on the relaxed circumference of the leg opening margin 33 being about 10% smaller than the lower end of the range of leg circumferences of wearers for whom the diaper 20 is intended and the elastically extended circumference of the leg opening margin 33 being about 20% larger than the upper end of the range of leg circumferences of the intended wearers.

In addition to the advantages described above, a diaper 20 having highly elastically extensible leg opening margins 33 and/or highly elastically extensible outer leg cuffs 120 may be designed to have a smaller crotch region width 154 and less crotch region bulk than a diaper with conventional gathered outer leg cuffs. The crotch region 37 width 154 may be reduced without a negative effect on the ease of application and/or donning because the large elastic extensibility of the leg opening margins 33 makes it practical for the diaper 20 to have a large elastically extended overall flat lateral width 156. Minimization of the bulk in the crotch region 37 is advantageous because a wearer's crotch is narrow and excessive bulk in the crotch region 37 of the diaper 20 may cause discomfort. Also, the presence of excessive bulk may cause folding and/or lateral collapse of the crotch region 37 of the diaper 20, leading to leakage. The appearance of the diaper 20 during wear may also be degraded by such folding. As a result of these considerations, the crotch region 37 flat lateral width 154 in some embodiments preferably is equal to or less than about 30% of the overall flat lateral width 156 of the elastically extended diaper 20 and, in some embodiments, the crotch region 37 flat lateral width 154 preferably is equal to or less than about 25% of the overall elastically extended flat lateral width 156. In some embodiments, the crotch region 37 flat lateral width 154 may be as small as 10 mm.

The diaper 20 may also include at least one diagonal support member 200 as shown in FIG. 8. The diagonal support member 200 is designed to support the diaper 20 on the body substantially in the diagonal support zone, the anatomical location of which lies generally across the small of the back, over the hips, and across the lower abdomen of the wearer's body. In addition, the diaper 20 may also include at least one lateral reinforcement member 80 as shown in FIG. 8. The lateral reinforcement member 80 preferably laterally reinforces and/or supports the containment assembly 22 in the area across the lower abdomen of the body. Examples of the diagonal support member 200 and of the lateral reinforcement member 80 are described in copending and commonly assigned U.S. patent application Ser. No. 09/765,225 filed on Jan. 18, 2001 and entitled Disposable Absorbent Garment Having Improved Appearance and Sustained Fit, which is hereby incorporated herein by reference.

The disclosures of all patents, patent applications, and any corresponding patents which issue thereon, as well as any corresponding published foreign patent applications, and publications mentioned throughout this description are hereby incorporated herein by reference. It is expressly not admitted, however, that any of the documents incorporated herein by reference teach or disclose the present invention.

While various embodiments and/or individual features of the present invention have been illustrated and described, it would be obvious to those skilled in the art that various other changes and modifications can be made without departing from the spirit and scope of the invention. As will also be apparent to the skilled practitioner, all combinations of the embodiments and features taught in the foregoing disclosure are possible and can result in preferred executions of the invention. It is therefore intended to cover in the appended claims all such changes and modifications as are within the scope of this invention.

What is claimed is:

1. A pre-closed absorbent article for fitting about a wearer's body to contain excreta and/or bodily exudates, comprising:
    a containment assembly having a front waist region, a back waist region opposed to the front waist region, a crotch region disposed between the front waist region and the back waist region, a front end edge, a back end edge, side edges comprising portions defining leg openings when the absorbent article is closed, leg opening margins, a longitudinal centerline, a lateral centerline, a topsheet, a backsheet, and an absorbent core disposed as least partially between the topsheet and the backsheet,
    at least one of the leg opening margins having an elastic extensibility of at least about 60 percent when the absorbent article is elastically extended laterally by a 5 kg lateral spreading force applied at an uppermost distal point of each of the leg opening margins, and
    at least one outer leg cuff having an elastic extensibility of at least about 60 percent when the absorbent article is elastically extended laterally by the 5 kg lateral spreading force,
    wherein the outer leg cuff is wrapped over at least one of the portions of one of the side edges defining one of the leg openings.

2. The absorbent article of claim 1 wherein as least a portion of the outer leg cuff is curved.

3. The absorbent article of claim 1 wherein the outer leg cuff is discrete.

4. The absorbent article of claim 3 wherein the outer leg cuff has first and second ends joined to encircle at least one of the leg openings.

5. The absorbent article of claim 1 wherein the outer leg cuff comprises a laminate.

6. The absorbent article of claim 1 wherein the outer leg cuff is differentially elastically extensible.

7. The absorbent article of claim 6 wherein the outer leg cuff comprises at least a first portion having an elastic extensibility of at least about 100 percent.

8. The absorbent article of claim 1 wherein the leg opening margin is differentially elastically extensible.

9. The absorbent article of claim 8 further comprising at least one substantially straight discrete outer leg cuff wrapped over at least one of the portions of one of the side edges defining one of the leg openings, the outer leg cuff comprising a first end disposed in an upper front quadrant of a circumference of the one of the leg openings and a second end disposed in a back quadrant of the circumference of the one of the leg openings to at least partially encircle the one of the leg openings.

10. The absorbent article of claim 8 wherein the leg opening margin comprises at least three portions having differential elastic extensibility.

11. The absorbent article of claim 10 wherein at least one of the three portions of the leg opening margin has an elastic extensibility of at least about 100 percent.

12. The absorbent article of claim 1 wherein at least one of the leg openings has an orientation angle of about 30 degrees or less when, the absorbent article is elastically extended laterally by the 5 kg lateral spreading force.

13. The absorbent article of claim 1 having a crotch region flat lateral width equal to or less than about 30% of an overall flat lateral width of the absorbent article when the absorbent article is elastically extended laterally by the 5 kg lateral spreading force.

14. The absorbent article of claim 1 further comprising at least one outer leg cuff comprising an incrementally stretched laminate having an elastic extensibility of at least about 60 percent when the absorbent article is elastically extended laterally by the 5 kg lateral spreading force.

15. The absorbent article of claim 14 wherein the outer leg cuff is folded such that a free edge of the outer leg cuff is disposed adjacent to an inner surface of the containment assembly.

16. The absorbent article of claim 15 wherein at least a portion of the outer leg cuff is continuous with the backsheet.

17. An absorbent article for fitting about a wearer's body to contain excreta and/or bodily exudates, comprising:
a containment assembly having a front waist region, a back waist region opposed to the front waist region, a crotch region disposed between the front waist region and the back waist region, a front end edge, a back end edge, side edges comprising portions defining leg openings when the absorbent article is closed, leg opening margins, a fastening system, a longitudinal centerline, a lateral centerline, a topsheet, a backsheet, and an absorbent core disposed at least partially between the topsheet and the backsheet,
at least one of the leg opening margins having an elastic extensibility of at least about 60 percent when the absorbent article is elastically extended laterally by a 5 kg lateral spreading force applied at an uppermost distal point of each of the leg opening margins.

18. The absorbent article of claim 17 wherein the leg opening margin is differentially elastically extensible.

19. The absorbent article of claim 18 wherein the leg opening margin comprises at least three portions having differential elastic extensibility.

20. The absorbent article of claim 18 further comprising at least one substantially straight discrete outer leg cuff wrapped over at least one of the portions of one of the side edges defining one of the leg openings, the outer leg cuff comprising a first end disposed in an upper front quadrant of a circumference of the one of the leg openings and a second end disposed in a back quadrant of the circumference of the one of the tag openings to at least partially encircle the one of the leg openings.

21. The absorbent article of claim 17 wherein at least one of the leg openings has an orientation angle of about 30 degrees or less when the absorbent article is elastically extended laterally by the 5 kg lateral spreading force.

22. The absorbent article of claim 17 having a crotch region flat lateral width equal to or less than about 30% of an overall flat lateral width of the absorbent article when the absorbent article is elastically extended laterally by the 5 kg lateral spreading force.

23. The absorbent article of claim 17 further comprising at least one outer leg cuff comprising an incrementally stretched laminate having an elastic extensibility of at least about 60 percent when the absorbent article is elastically extended laterally by the 5 kg lateral spreading force.

24. The absorbent article of claim 23 wherein at least a portion of the outer leg cuff is wrapped over at least one of the portions of one of the side edges defining one of the leg openings.

25. The absorbent article of claim 24 wherein the outer leg cuff is folded such that a free edge of the outer leg cuff is disposed adjacent to an inner surface of the containment assembly.

26. The absorbent article of claim 25 wherein at least a portion of the outer leg cuff is continuous with the backsheet.

27. A pre-closed absorbent article for fitting about a wearer's body to contain excrete and/or bodily exudates, comprising:
   a) a containment assembly having a front waist region, a back waist region opposed to the front waist region, a crotch region disposed between the front waist region and the back waist region, a front end edge, a back end edge, side edges comprising portions defining leg openings when the absorbent article is closed, leg opening margins, a longitudinal centerline, a lateral centerline, a topsheet, a backsheet, and an absorbent core disposed at least partially between the topsheet and the backsheet, at least one of the leg opening margins having an elastic extensibility of at least about 60 percent when the absorbent article is elastically extended laterally by a 5 kg lateral spreading force applied at an uppermost distal point of each of the leg opening margins; and
   b) at least one curved discrete outer leg cuff having an elastic extensibility of at least about 60 percent when the absorbent article is elastically extended laterally by the 5 kg lateral spreading force, the outer leg cuff being wrapped over at least one of the portions of one of the side edges defining one of the leg openings, the outer leg cuff comprising first and second ends joined to encircle at least one of the leg openings.

28. An absorbent article for fitting about a wearer's body to contain excreta and/or bodily exudates, comprising:
a containment assembly having a front waist region, a back waist region opposed to the front waist region, a crotch region disposed between the front waist region and the back waist region, side edges comprising portions defining leg openings when the absorbent article is closed, leg opening margins, a topsheet, a backsheet, and an absorbent core disposed at least partially between topsheet and the backsheet, and
at least one outer lee cuff comprising an incrementally stretched laminate, wherein at least a portion of the outer leg cuff is wrapped over at least one of the portions of one of the side edges defining one of the leg openings.

29. An absorbent article for fitting about a wearer's body to contain excreta and/or bodily exudates, comprising:

a containment assembly having a front waist region, a back waist region opposed to the front waist region, a crotch region disposed between the front waist region and the back waist region, side edges comprising portions defining leg openings when the absorbent article is closed, leg opening margins, a topsheet, a backsheet and an absorbent core disposed at least partially between the topsheet and the backsheet, and at least one outer leg cuff comprising an incrementally stretched laminate, wherein at least a portion of the outer leg cuff is wrapped over at least one of the portions of one of the side edges defining one of the leg openings, and wherein the outer leg cuff is folded such that a free edge of the outer leg cuff is disposed adjacent to an inner surface of the containment assembly.

30. An absorbent article for fitting about a wearer's body to contain excrete and/or bodily exudates, comprising:

a containment assembly having a front waist region a back waist region opposed to the front waist region, crotch region disposed between the front waist region and the back waist region, side edges comprising portions defining leg openings when the absorbent article is closed, leg opening margins, a topsheet, a backsheet, and an absorbent core disposed at least partially between the topsheet and the backsheet, and at least one outer leg cuff comprising an incrementally stretched laminate, wherein least a portion of the outer leg cuff is wrapped over at least one of the portions of one of the side edges defining one of the leg openings, and wherein the outer leg cuff is folded such that a free edge of the outer leg cuff is disposed adjacent to an inner surface of the containment assembly, and wherein at least a portion of the outer leg cuff is continuous with the backsheet.

31. A pre-closed absorbent article for fitting about a wearer's body to contain excrete and/or bodily exudates, comprising:

a containment assembly having a front waist region, a back waist region opposed to the front waist region, a crotch region disposed between the front waist region and the back waist region, side edges comprising portions defining leg openings when the absorbent article is closed, leg opening margins, a topsheet a backsheet, and an absorbent core diagnosed at least partially between the topsheet and the backsheet, and at least one outer leg cuff comprising an incrementally stretched laminate, wherein at least a portion of the outer leg cuff is wrapped over at least one of the portions of one of the side edges defining one of the leg openings.

32. A pre-closed absorbent article for fitting about a wearer's body to contain excreta and/or bodily exudates, comprising:

a containment assembly having a front waist region, a back waist region opposed to the front waist region, a crotch region disposed between the front waist region and the back waist region, side edges comprising portions defining leg openings when the absorbent article is closed, leg opening margins, a topsheet, a backsheet, and an absorbent core disposed at least partially between the topsheet and the backsheet, and at least one outer leg cuff comprising an incrementally stretched laminate, wherein at least a portion of the outer leg cuff is wrapped over at least one of the portions of one of the side edges defining one of the lee openings, and wherein the outer leg cuff is folded such that a free edge of the outer leg cuff is disposed adjacent to an inner surface of the containment assembly.

33. A pre-closed absorbent article for fitting about a wearer's body to contain excreta and/or bodily exudates comprising:

a containment assembly having a front waist region, a back waist region opposed to the front waist region, a crotch region diseased between the front waist region and the back waist region, side edges comprising portions defining leg openings when the absorbent article is closed, leg opening margins, a topsheet, a backsheet, and an absorbent core disposed at least partially between the topsheet and the backsheet, and at least one outer leg cuff comprising incrementally stretched laminate, wherein at least a portion of the outer leg cuff is wrapped over at least one of the portions of one of die side edges defining one, of the leg openings, and wherein the outer leg cuff is folded such that a free edge of the outer leg cuff is diseased adjacent to an inner surface of the containment assembly, and wherein as least a portion of the outer leg cuff is continuous with the backsheet.

* * * * *

UNITED STATES PATENT AND TRADEMARK OFFICE
CERTIFICATE OF CORRECTION

PATENT NO. : 6,764,478 B2
DATED : July 20, 2004
INVENTOR(S) : Gregory Ashton et al.

It is certified that error appears in the above-identified patent and that said Letters Patent is hereby corrected as shown below:

Column 16,
Lines 43 and 57, delete "as least" and insert therefor -- at least --.

Column 17,
Line 23, delete "when, the" and insert therefor -- when the --.

Column 18,
Line 4, delete "tag openings" and insert therefor -- leg openings --.
Line 31, delete "excrete" and insert therefor -- excreta --.
Line 66, delete "lee cuff" and insert therefor -- leg cuff --.

Column 19,
Lines 24 and 45, delete "excrete" and insert therefor -- excreta --.

Column 20,
Line 1, delete "diagnosed" and insert therefor -- disposed --.
Line 25, delete "lee openings" and insert therefor -- leg openings --.
Line 34, delete "diseased" and insert therefor -- disposed --.
Line 44, delete "die side edges defining one, of" and insert therefor -- the side edges defining one of --.
Line 47, delete "diseased " and insert therefor -- disposed --.

Signed and Sealed this

First Day of February, 2005

JON W. DUDAS
*Director of the United States Patent and Trademark Office*